United States Patent [19]

Ohloff et al.

[11] 4,009,127

[45] Feb. 22, 1977

[54] OXATRICYCLO COMPOUNDS USEFUL AS PERFUMING AGENTS

[75] Inventors: Günther Ohloff; Wolfgang K. Giersch, both of Bernex, Switzerland

[73] Assignee: Firmenich S.A., Geneva, Switzerland

[22] Filed: June 20, 1975

[21] Appl. No.: 588,909

[30] Foreign Application Priority Data

June 21, 1974 Switzerland .................... 8516/74

[52] U.S. Cl. .................. 252/522; 260/346.2 M
[51] Int. Cl.$^2$ .................................. C07D 307/77
[58] Field of Search ............ 260/346.2 M; 252/522

[56] References Cited

OTHER PUBLICATIONS

Sanderman et al., Parfumerie and Kosmetik, vol. 54, pp. 335–339 (1973).

*Primary Examiner*—Natalie Trousof
*Assistant Examiner*—Bernard Dentz
*Attorney, Agent, or Firm*—Pennie & Edmonds

[57] ABSTRACT

New oxygenated tricyclic derivatives are disclosed as being useful as perfuming and flavoring agents for the preparation of perfumes and perfumed articles and for the manufacture of artificial flavors, flavored foodstuffs, animal feeds, beverages, pharmaceutical preparations and tobacco products.

7 Claims, No Drawings

OXATRICYCLO COMPOUNDS USEFUL AS PERFUMING AGENTS

SUMMARY OF THE INVENTION

The compounds to which the invention relates have the formula (I):

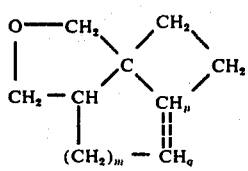

wherein:
a. $m = 6$, $p = 0$ or $1$, $q = 1$ or $2$;
b. $m = 7$, $p = 0$ or $1$, $q = 1$ or $2$; or
c. $m = 8$, $p = 0$ or $1$, $q = 1$ or $2$
and in which the dotted lines represent a single or a double bond.

The invention relates further to the use of said compounds of formula (I) as flavouring agents for the preparation of artificial flavour compositions and for the aromatization of foodstuffs, animal feeds, beverages, pharmaceutical preparations and tobacco products, and/or perfuming agents for the manufacture of perfumes, perfuming compositions and perfumed articles.

The present invention also relates to a process for the preparation of the said compounds of formula (I).

BACKGROUND OF THE INVENTION

In the art of perfumery, substances possessing an odoriferous amber-like note have always been regarded as being of primary interest. In most cases these substances find an extensive use in the preparation of a great variety of perfume compositions of different nature, namely for the fine perfume compositions.

The amber fragrance acts as a fixative on most of the commonly used perfuming ingredients and possesses an amplifying effect when used in "Chypre"-, "Fougere"-, flowery-, woody-, leathery-, oriental- or animal-type compositions wherein it increases at the same time their diffusiveness. In modern perfume compounding the amber fragrance is particularly appreciated in perfume compositions for men perfume lines. Until the 1940's, ambergris, a product of animal origin, represented one of the few substances used for reproducing the typical amber fragrance. Its availability is however extremely poor and consequently its price particularly high. Following the extensive investigations carried out by Ruzicka — cf. Helv. Chim. Acta 29, 912 (1946) — and by Lederer — cf. Helv. Chim. Acta 29, 1354 (1946) — on the structure of ambreine, which is one of the major constituents of ambergris, the chemical industry undertook a great deal of effort in order to synthesize new chemical species able to develop an amber odour. The chemical literature contains numerous references to bicyclic or tricyclic derivatives, namely derived from sclareol or from manool — cf. W. Sandermann and R. Casken, Parfumerie und Kosmetik 54, 335 (1973) —. Nowadays, most commercially available amber-type products consist of a mixture of materials simulating the odour of ambergris and are sold under various trade names.

PREFERRED EMBODIMENTS OF THE INVENTION

It has now been found that the compounds of the invention possess interesting organoleptic properties and, accordingly, are useful as perfuming and odour-modifying agents, and as flavouring and taste-modifying agents.

They can be compounded with other odoriferous substances, to make perfume compositions, in the manner conventional in the perfumery art; they can be used, combined with carriers or diluents, for perfuming a wide range of products such as soaps, detergents, house-hold materials or cosmetic articles. The compounds of formula (I) develop a well distinct, intense and clinging amber fragrance. This odour matches particularly well, e.g. with woody, flowery, animal or musky perfume notes; their use is therefore very wide.

In perfumery the compounds of the invention can be used at concentrations varying within wide limits. Interesting effects can be achieved at concentrations of from about 0.1 to 10%, or even 20%, by weight based on the total weight of the perfumed composition. Proportions lower than 0.1% or higher than 20% can also be used, viz. when the compounds of formula (I) are used as reinforcers in perfume base or perfume "coeurs." The preferred concentrations are however of the order of about 1%.

When used as flavouring agents, the tricyclic compounds of formula (I) can develop a typical amber-woody gustative note. This character, which is reminiscent of that developed by sandal-wood, possesses a fruity and musky tonality whose intensity is more or less developed according to the case.

Accordingly, compounds (I) are particularly suited for the preparation of various artificial flavour compositions destined to the aromatization of foodstuffs and beverages in general. More particularly, they find a useful application in the aromatization of tobacco and tobacco products wherein the woody, amber and, at the same time, musky note is widely appreciated.

To this effect, the compounds of the invention may be used in a variety of forms, but they are preferably used in solution. A convenient method for flavouring tobacco consist in spraying it with a solution of the flavouring compound, or the composition containing it, in alcohol or a mixture of alcohol and propylene glycol.

The proportions in which the flavouring agents of the invention are used in flavouring compositions or are added to an article to be flavoured can vary widely, depending upon the specific organoleptic effect it is desired to achieve.

In the aromatisation of tobacco or tobacco products interesting flavouring effects can be achieved with amounts ranging from about 0.1 to 10 parts per million (ppm) based on the total weight of the flavoured product, preferably from about 1 to 5 ppm. However, amounts of less than 0.1 ppm or amounts of more than 10 ppm can be used when specific flavouring effects are to be achieved.

In accordance with the present invention, the compounds of formula (I) are prepared by a process which comprises reacting a bicyclic compound of formula (II)

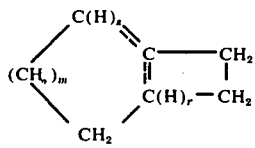

(II)

containing a double bond in one of the positions indicated by the dotted lines and wherein:

a. m = 6, r = 0, s = 2 or r = s = 1;
b. m = 7, r = 0, s = 2 or r = s = 1, or
c. m = 8, r = 0, s = 2 or r = s = 1; with a mixture of acetic acid and paraformaldehyde in the presence of a strong mineral or organic acid and, if desired, reducing the thus obtained unsaturated compound to give the corresponding saturated derivative.

Compounds (II), used as starting materials in the above described process, can be synthesized in accordance with the conventional methods as better illustrated hereinafter in the given Examples.

According to the invention the compounds of formula (I) can also be prepared by a process which comprises a. reacting a bicyclic compound of formula (II) with paraformaldehyde in the presence of acetic anhydride and catalytic amounts of a Lewis acid, b. treating the reaction mixture with an alkali metal hydroxide in an alcoholic solution, and subsequently c. cyclising the thus obtained alcohol in the presence of paraformaldehyde, acetic acid and a strong organic acid at a temperature of from about 70° to 100° C.

The process described above is better illustrated by the following reaction scheme

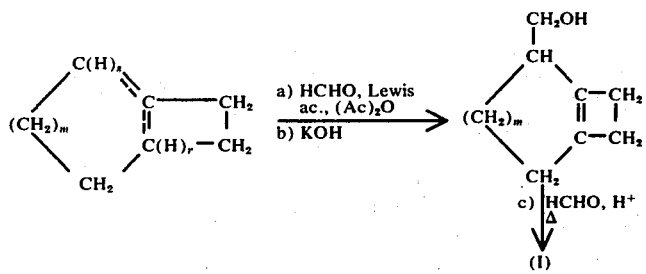

According to a preferred embodiment of the process of the present invention, the compounds of formula (II) are reacted with a mixture comprising acetic acid and paraformaldehyde in a weight ratio of from about 10:1 to 10:4. The acetic acid can be conveniently replaced by a mixture of acetic acid and acetic anhydride wherein this latter is present in a proportion of about 1 to 5%. Suitable strong acids include sulfuric acid, benzenesulphonic or p-toluenesulphonic acid.

When p-toluenesulphonic acid is used, the reaction may be effected at a temperature of from about 80° C to the boiling temperature of the chosen mixture of acetic acid/paraformaldehyde, e.g. 110° C. Preferably, the reaction is carried out at about 100° C in much the same way as that followed for analogous reactions on monocyclic olefines — cf. Liebigs Ann. Chem. 1973, 1797 —.

On the contrary, when sulfuric acid is used, is is preferred to operate at temperatures of from about 20° to 40° C, more preferably in the vicinity of 40° C — cf. Bull. Chem. Soc. Japan 46, 2512 (1973) —.

As an example, 3-oxa-tricyclo[11.3.0.01,14]hexadec-13-ene can be obtained in good yields by the process of the invention when bicyclo[9.2.0]tridec-1(4)-ene or bicyclo[9.2.0]tridec-13-ene is used as the starting material.

The unsaturated oxygenated tricyclic compounds obtained in accordance with the process described above are, if desired, reduced to their corresponding saturated derivatives according to the usual techniques, preferably by catalytic hydrogenation in the presence, for example, of platinum oxide, Raney nickel or palladium on charcoal.

Thus, 3-oxa-tricyclo[11.3.0.0$^{1,14}$]hexadec-13-ene in ethanol solution can be hydrogenated to 3-oxa-tricyclo[11.3.0.0$^{1,14}$]hexadecane in the presence of palladium on charcoal.

Suitable Lewis acids include $BF_3$, $AlCl_3$, $SnCl_4$, for example. As a strong organic acid, p-toluenesulphonic is preferred. Step (a) of the said process, is preferably carried out at room temperature in the presence of an inert organic solvent. Suitable solvents include halogenated hydrocarbons such as methylene chloride, ethylene chloride, chloroform and tetrachloroethylene.

The invention is better illustrated by but not limited to the following Examples wherein the temperatures are given in degrees centigrade and the abbreviations have the conventional meaning in the art.

EXAMPLE 1

3-Oxa-tricyclo[11.3.0.0$^{1,14}$]hexadec-13-ene

A mixture of 100 g (0.56 M) of bicyclo[9.2.0]tridec-1(4)-ene, 100 g of acetic acid, 30 g (1.00 M) of paraformaldehyde and 6 g of p-toluenesulphonic acid was heated at 100° for 5 h. After cooling to room temperature, the reaction mixture was diluted with 500 ml of water and extracted with 3 fractions of 200 ml each of ether. The obtained organic phase was then washed with a 10 % aqueous solution of $NaHCO_3$, then with a 10 % aqueous solution of NaOH until neutrality. After evaporation of the volatile portions and fractional distillation of the obtained residue, 72 g of a product having b.p. 105°–120° / 0.05 Torr containing 61% of the desired tricyclic compound were obtained. An analytical sample was obtained by purification by means of a fractional distillation on a spinning band column.

IR (neat): 920 cm$^{-1}$

NMR (90 MHz, CDCl$_3$): 0.90–2.10 (15H, m); 2.15–2.90 (4H, m); 3.30 (1H, d of d, $J_1$ = 8, $J_2$ = 11 cps); 3.65–4.10 (3H, m); 5.28 (1H, m) δ ppm MS: M$^+$ = 220 (2); m/e: 191 (10), 146 (20), 117 (74), 115 (43), 99 (49), 91 (100), 77 (24), 71 (30), 55 (53), 43 (64), 41 (56).

Bicyclo[9.2.0]tridec-1(4)-ene used as starting material in the above described process was obtained as indicated hereinafter:

a. *cyclotridecanone:* 200 ml of a 50% aqueous solution of NaOH were added dropwise under vigorous stirring to a mixture of 132 g of cyclododecene (CHEMICAL SAMPLE Co - Columbus, Ohio - USA), 600 g of bromoform and 4 g of tetramethylammonium bromide. The mixture was then left at a temperature between 40° and 50° under stirring during 2 h, whereupon it was left at room temperature overnight and diluted with water. Finally the reaction mixture was extracted with 3 fractions of 300 ml each of ether. The combined extracts, after the usual treatments of washing, drying and evaporation, gave a residue which upon fractional distillation under reduced pressure yielded 173 g (92%) of 2,2-dibromo-bicyclo[10.1.0]tridecane.

20 g of this compound were heated in a sealed tube for 5 h at 150°. The mixture was then distilled under reduced pressure (0.1 Torr) to give 18.5 g (92%) of 1,13-dibromo-cyclotridec-1-ene.

15 g of the thus obtained compound were dissolved in 50 ml of anhydrous ether and the solution was slowly added to a suspension of 2 g of LiAlH$_4$ in 50 ml of anhydrous ether. After addition of the reactants, stirring was maintained for 16 h while the temperature was kept at 20°. The reaction mixture was then poured into ice, and extracted with ether. After the usual treatments, the organic phase gave 10.8 g (94 %) of 1-bromo-cyclotridec-1-ene; b.p. 71°–75°/0.1 Torr.

10 g of the bromo derivative obtained above were mixed at 0° with 50 g of concentrated H$_2$SO$_4$ also cooled at 0° before addition. The reaction mixture was then slowly brought to 20° and kept at this temperature for 3 h, then poured onto ice and extracted with ether. The usual treatments of the organic phase followed by a fractional distillation gave 7.1 g (94%) of cyclotridecanone; b.p. 82°/0.1 Torr.

b. bicyclo[9.2.0]tridecan-1-ol: a 5% solution cyclotridecanone in cyclohexane was irradiated at 20° by using a mercury vapour lamp of 2000 Watt enclosed in quartz vessel until complete disappearance of the starting material. After evaporation of the volatile fractions followed by distillation of the residue under vacuum, there was isolated in 67% yield the desired bicyclic alcohol whose analytical properties were in all respects identical to those of the compound prepared in accordance with Bull. Chem. Soc. Japan 44, 3440 (1971).

c. bicyclo[9.2.0]tridec-1(4)-ene: 10 g of the above obtained bicyclic alcohol were dehydrated by means of a mixture of pyridine/thionyl chloride according to the procedure described in the above mentioned literature. The bicyclic olefin was obtained with a 90% yield.

Bicyclo[9.2.0]tridec-1(4)-ene can also be obtained with a yield of approximately 95 % according to the following procedure:

1 equivalent of the bicyclic alcohol obtained according to the method described sub letter b) above and 2 equivalents of boric acid were intimately mixed and heated at 100° under vacuum (15 Torr). The residue obtained was then distilled by heating the vessel at 140°–160°/0.5 Torr and gave the desired bicyclic olefin.

EXAMPLE 2

3-Oxa-tricyclo[11.3.0.0$^{1,14}$]hexadecane 2.2 g (0.01 M) of the tricyclic derivative obtained in accordance with Example 1 in 20 ml of ethanol were hydrogenated in the presence palladium on charcoal. By filtration of the reaction mixture, evaporation and fractional distillation of the residue there were obtained 2.1 g (95 %) of the title compound.

IR (neat): 928 cm$^{-1}$
NMR (90 MHz, CDCl$_3$): 0.80–2.60 (22H, m); 3.28 (1H, d of d, J$_1$ = 8, J$_2$ = 8 cps); 3.60–4.20 (3H, m) δ ppm
MS: M$^+$ = 222 (1); m/e: 109 (21), 95 (54), 83 (74), 82 (100), 81 (54), 69 (45), 67 (50), 55 (72), 41 (76).

EXAMPLE 3

3-Oxa-tricyclo[10.3.0.0$^{1,13}$]pentadec-12-ene

This compound was obtained in a 33% yield starting from bicyclo[8.2.0]dodec-1(4)-ene in the same conditions as those described in Example 1 for the preparation of 3-oxa-tricyclo[11.3.0.0$^{1,14}$]hexadec-13-ene.

An analytical sample was prepared by purifying the obtained compound by distillation on spinning band column. Starting bicyclo[8.2.0]dodec-1(4)-ene was obtained from cyclododecanone by irradiation and dehydration as indicated in Example 1 sub letters (a) to (c). The title compound showed the following analytical data:

IR (neat): 2900, 1460, 1070, 1045, 940, 930 cm$^{-1}$
NMR (90MHz, CCl$_4$): 1.40 (10H, broad s); 1.6–2.8 (7H, m); 3.2–4.2 (4H, m); 5.35–5.65 (1H, m) δ ppm
MS: M$^+$ = 206 (27); 191 (3), 177 (28), 149 (22), 135 (30), 133 (27), 121 (29), 119 (32), 109 (33), 107 (39), 105 (47), 95 (61), 93 (64), 91 (94), 81 (68), 79 (93), 67 (73), 55 (58), 41 (100).

EXAMPLE 4

3-Oxa-tricyclo[12.3.0.0$^{1,15}$]heptadec-14-ene 10 g of bicyclo[10.2.0]tetradec-1(4)-ene were converted into the desired tricyclic compound in a 30 % yield by treating them in accordance with the reaction conditions described in Example 1 by using a mixture of acetic acid/paraformaldehyde/p-toluenesulphonic acid.

An analytical sample was prepared by distilling the obtained product on a spinning band column.

IR (neat): 925 cm$^{-1}$
NMR (60 MHz, CCl$_4$): 0.80–2.80 (21H, m); 3.13 (d of d, J$_1$ = 8, J$_2$ = 10 cps, 1H); 3.50–4.00 (3H, m); 5.22 (1H, m,w½ = 10 cps) δ ppm
MS: M$^+$ = 234 (23); m/e: 205 (67), 135 (33), 121 (43), 109 (61), 95 (73), 93 (70), 91 (63), 81 (71), 79 (80), 67 (70), 55 (65), 41 (100).

Bicyclo[10.2.0]tetradec-1(4)-ene used as starting material in the above given process was obtained from cyclododecanone according to the process described in Comptes Rendus Acad. Sciences, Paris, 279, 305 (1972).

EXAMPLE 5

3-Oxa-tricyclo[11.3.0.0$^{1,14}$]hexadec-13-ene

A solution of 20 ml of acetic anhydride and 0.5 ml of BF$_3$ etherate in 20 ml of dichloromethane was added dropwise to a mixture of 12 g F(67.5 mM) of bicyclo[9.2.0]tridec-1(4)-ene, 2 g (67 mM) of paraformaldehyde, 30 ml of acetic anhydride and 30 ml of dichloromethane. During the whole addition (90 min.) the reaction mixture was kept under vigorous stirring, while the temperature rose to 33° whereupon the stirring was maintained for 1 supplemental hour and the temperature decreased till 25°. After extraction with ether followed by the usual treatments of the separated organic phase, there was obtained a residue which was subjected to saponification by means of treatment with NaOH in methanolic solution during one hour at reflux. Extraction with ether and the usual treatments gave 13.6 g of 2-hydroxymethyl-bicyclo[9.2.0]tridec-1(11)-ene. The purification of the obtained alcohol was carried out by a column chromatography on $SiO_2$ by using a 4:1 mixture of hexane/ether as the eluent.

IR: 3350 $cm^{-1}$

NMR: 1.33 (s, 14 H), 1.82 (s, 1H), 2.27 (s, 4H), 3.35 (d, J = 7 cps, 2H) δ ppm

MS: $M^+$ 208 (13), m/e 177 (13), 135 (15), 121 (18), 109 (22), 95 (100), 81 (74), 67 (64), 55 (50), 41 (61), 29 (30).

A mixture of the alcohol obtained as indicated above (1 g), 0.2 g of paraformaldehyde, 0.1 g of p-toluenesulphonic acid and 10 ml of acetic acid in the presence of a few drops of acetic anhydride was heated for 4½ hour at 95° while stirring. The usual treatments of extraction, separation, drying, and evaporation gave 0.7 g of a product which was distilled on a bulb apparatus. The purity of the thus obtained compound was of about 95 % as shown by gas chromatographic analysis. This compound was in all respects identical to that prepared in Example 1.

EXAMPLE 6

A base perfume composition of the Chypre type was obtained by admixing the following ingredients (parts by weight):

| | |
|---|---|
| 1,1-Dimethyl-4-acetyl-6-ter-butylindane | 50 |
| Synth. Jasmin | 50 |
| Synth. Rose | 50 |
| Labdanum oil 10%* | 20 |
| Musk ketone | 50 |
| Coumarin | 50 |
| Patchouli oil | 30 |
| Vetyver Bourbon oil | 50 |
| Phenyl-ethyl alcohol | 100 |
| Citronellol | 80 |
| Hexylcinnamic aldehyde | 100 |
| Benzyl acetate | 50 |
| Petitgrain Bigarade oil | 30 |
| Ylang oil | 50 |
| Synth. Bergamot | 100 |
| Methyl-nonylacetic aldehyde 10%* | 25 |
| Orange oil | 50 |
| Ethylvanillin | 5 |
| Linalool | 60 |
| Total | 1000 |

*in diethyl phthalate

The obtained perfume base possessed a tonality which was at the same time spicy and amber-like, analogous to that shown in men-type Eau de Cologne for example.

By adding to 95 g of the above base 5 g of 3-oxa-tricyclo[11.3.0.0$^{1,14}$]hexadec-13-ene there was obtained a novel perfume composition which showed a reinforced amber character and possessed more distinction than the base composition. By substituting one of the homologous tricyclic ethers described in Examples 3 and 4 for 3-oxa-tricyclo[11.3.0.0$^{1,14}$]hexadec-13-ene analogous effects were observed. However, certain variations were noticeable with regard to the tenacity of the obtained fragrances which was in this case more or less pronounced.

EXAMPLE 7

A base perfume composition was prepared by mixing the following ingredients (parts by weight):

| | |
|---|---|
| Synth. Bergamot oil | 100 |
| α-Iso-methylionone | 90 |
| Decolorized absolute oak-moss 50%* | 80 |
| Sweet orange oil | 80 |
| Vetyveryl acetate | 80 |
| p-ter-Butyl-cyclohexyl-acetate | 80 |
| Angelica roots oil 10 %* | 50 |
| Musk Ambrette | 50 |
| Lavender oil | 30 |
| Cade oil (dephenolated) | 30 |
| Synth. Castoreum | 30 |
| Clary sage oil | 30 |
| Sandal wood oil | 20 |
| Eugenol | 20 |
| Iso-eugenol | 20 |
| Costus oil 10 %* | 20 |
| Synth. pepper oil | 20 |
| Absolute Eau de feuilles d'oranger 10 %* | 20 |
| Italian lemon oil | 20 |
| Synth. Neroli oil | 10 |
| Galbanum oil | 10 |
| Citral | 10 |
| Total | 900 |

*in diethyl phthalate

By adding to 90 g of the above base composition 10 g of a 10% solution of 3-oxa-tricyclo[11.3.0.0$^{1,14}$]hexadec-13-ene in diethyl phthalate there was obtained a novel composition which possessed a richer, deeper, and more rounded amber-like fragrance.

EXAMPLE 8

35 mg of a 0.1% solution of 3-oxa-tricyclo[11.3.0.0$^{1,14}$]hexadec-13-ene in 95% ethanol were sprayed on 100 g of a mixture of American Blend type tobacco. The aromatized tobacco was used for manufacturing test cigarettes the smoke of which was tested by a panel of experienced flavourists. By comparison of their taste and aroma with those of the cigarettes manufactured with tobacco treated with an equal proportion of 95% ethanol, the panel established that smoke of the test cigarettes possessed a more marked woody and amber-like note than the smoke of the unflavoured cagarettes.

By replacing in the above example 3-oxa-tricyclo[11.3.0.0$^{1,14}$]hexadec-13-ene by one of the homologous tricyclic ethers prepared in Example 3 and 4, analogous results were obtained.

What we claim is:

1. A compound of formula (I)

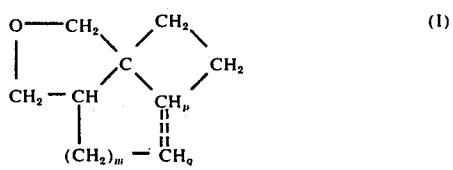

wherein:
a. m = 6, p = 0 or 1, q = 1 or 2;
b. m = 7, p = 0 or 1, q = 1 or 2; or
c. m = 8, p = 0 or 1, q = 1 or 2 and in which the dotted lines represent a single or a double bond.

2. 3-Oxa-tricyclo[10.3.0.0$^{1,13}$]pentadec-12-ene.
3. 3-Oxa-tricyclo[11.3.0.0$^{1,14}$]hexadec-13-ene.
4. 3-Oxa-tricyclo[11.3.0.0$^{1,14}$]hexadecane.
5. 3-Oxa-tricyclo[12.3.0.0$^{1,15}$]heptadec-14-ene.
6. A perfume composition comprising an effective amount of a compound of formula (I), as defined in claim 1, and a perfume base.
7. A method for improving, enhancing or suitably modifying the odoriferous properties of a perfume or perfumed product, which comprises adding thereto in effective amounts at least one compound of formula (I), as defined in claim 1.

* * * * *